United States Patent [19]
Ross et al.

[11] Patent Number: 6,121,268
[45] Date of Patent: Sep. 19, 2000

[54] BENZYLOXY SUBSTITUTED AROMATICS AND THEIR USE AS FUNGICIDES

[75] Inventors: Ronald Ross, Jamison; Ted Tsutomo Fujimoto, Churchville; Edward Michael Szapacs, Center Valley; Steven Howard Shaber, Horsham, all of Pa.

[73] Assignee: Rohm and Haas Company, Philadelphia, Pa.

[21] Appl. No.: 09/197,637

[22] Filed: Nov. 23, 1998

Related U.S. Application Data

[60] Provisional application No. 60/066,455, Nov. 24, 1997.

[51] Int. Cl.[7] .................. C07C 271/12; C07C 271/14; A01N 37/08; A01N 37/12; A01N 43/40
[52] U.S. Cl. .................. 514/256; 514/354; 514/355; 514/438; 514/448; 514/530; 514/531; 514/539; 544/335; 546/315; 546/328; 546/335; 549/72; 549/77; 560/27
[58] Field of Search .................. 514/256, 354, 514/355, 438, 448, 530, 531, 539; 544/335; 546/315, 328, 335; 549/72, 77; 560/27

[56] References Cited

U.S. PATENT DOCUMENTS 5,650,434   7/1997   Ohnishi et al. .
5,886,015   3/1999   Ross et al. .............. 514/378

FOREIGN PATENT DOCUMENTS

0619301A2   10/1994   European Pat. Off. .
WO 93/15046   8/1993   WIPO .

*Primary Examiner*—Samuel Barts
*Assistant Examiner*—Brian J. Davis
*Attorney, Agent, or Firm*—Thomas D. Rogerson

[57] ABSTRACT

Compounds with fungicidal properties having formula I

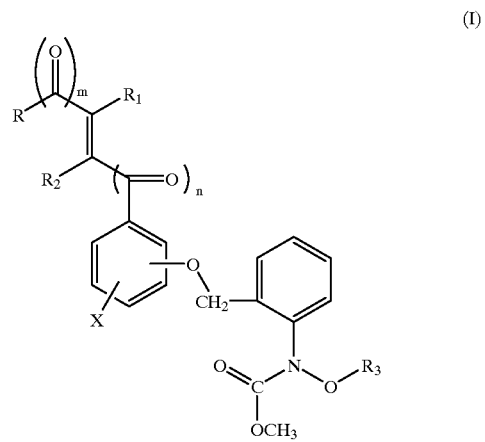

where m and n are 0 or 1 provided that m+n is 1; X is hydrogen, halo, $(C_1-C_4)$alkyl, or $(C_1-C_4)$alkoxy; R is an optionally-substituted alkyl, cycloalkyl, alkenyl, alkynyl, alkoxy, aryl, aralkyl, or heterocyclic group; $R_1$ and $R_2$ are hydrogen, optionally-substituted alkyl, cycloalkyl, cyano, carboxy alkyl, or aryl; at least one of $R_1$ and $R_2$ is hydrogen; and $R_3$ is alkyl or haloalkyl.

9 Claims, No Drawings

BENZYLOXY SUBSTITUTED AROMATICS AND THEIR USE AS FUNGICIDES

This application claims priority from Provisional Application No. 60/066,455 filed on Nov. 24, 1997.

The present invention relates to benzyloxy substituted phenyl compounds, compositions containing these compounds and methods for controlling fungi by the use of a fungitoxic amount of these compounds.

It is known that carbamates of certain benzyloxy substituted phenyl compounds are useful as fungicides. The substitution of the phenyl ring is known in the art (see for example WO93 15046). The problem addressed by the invention is the provision of further fungicidal compounds.

We have discovered phenyl derivatives which possess an acyl substituent to which is bonded an unsaturated group or an unsaturated group to which is bonded an acyl group. These novel compounds possess fungicidal properties.

The novel benzyloxy substituted phenyl compounds of the present invention have the Formula (I)

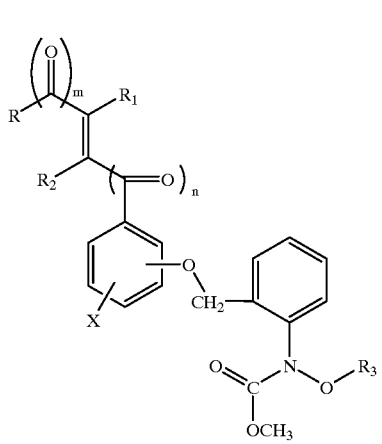

wherein
- m and n are integers 0 and 1, provided that m+n is 1;
- X is independently selected from hydrogen, halo, ($C_1$–$C_4$) alkyl, ($C_1$–$C_4$)alkoxy and —HC=CH—CH=CH— thereby forming a napthyl ring;
- R is independently selected from hydrogen, ($C_1$–$C_{12}$) alkyl, halo($C_1$–$C_{12}$)alkyl, ($C_2$–$C_{12}$)alkenyl, halo($C_2$–$C_{12}$)alkenyl, ($C_2$–$C_{12}$)alkynyl, halo($C_2$–$C_{12}$)alkynyl, ($C_{1-12}$)alkoxy($C_1$–$C_{12}$)alkyl, ($C_3$–$C_7$) cycloalkyl, halo($C_3$–$C_7$)cycloalkyl, ($C_3$–$C_7$)cycloalkyl ($C_1$–$C_4$)alkyl, aryl($C_3$–$C_7$)cycloalkyl, aryl, aralkyl, and heterocyclic; and
- $R_1$ and $R_2$ are independently selected from hydrogen, ($C_1$–$C_{12}$)alkyl, halo($C_1$–$C_{12}$)alkyl, ($C_3$–$C_7$)cycloalkyl, ($C_3$–$C_7$)cycloalkyl($C_1$–$C_4$)alkyl, cyano, carboxy ($C_1$–$C_4$)alkyl, aryl and $R_3$ is independently selected from ($C_1$–$C_{12}$)alkyl and halo($C_1$–$C_{12}$)alkyl; provided that $R_1$ or $R_2$ must be hydrogen.

The aforementioned ($C_1$–$C_{12}$)alkyl, ($C_2$–$C_{12}$)alkenyl, ($C_2$–$C_{12}$)alkynyl and ($C_3$–$C_7$)cycloalkyl groups may be optionally substituted with up to three substituents selected from the group consisting of nitro, halomethyl, ($C_1$–$C_4$) alkoxycarbonyl, and cyano.

As used herein, the term "alkyl" includes both branched and straight chain, substituted and unsubstituted, aliphatic hydrocarbon groups (generally having from 1 to 12 carbon atoms). Typical alkyl groups are methyl, ethyl, n-propyl, isopropyl, n-butyl, sec-butyl, isobutyl, t-butyl, n-pentyl, isopentyl, n-hexyl, n-heptyl, isooctyl, nonyl, decyl, undecyl, dodecyl and the like. The term "haloalkyl" refers to an alkyl group substituted with 1 to 3 halogens.

As used herein, the term "alkoxy" includes both branched and straight chain alkyl groups (generally having from 1 to 12 carbon atoms) having a terminal one oxygen atom. Typical alkoxy groups are methoxy, ethoxy, n-propoxy, iso-propoxy, n-butoxy, sec-butoxy isobutoxy, t-butoxy, n-pentoxy, isopentoxy, n-hexoxy, n-heptoxy and the like. The term "haloalkoxy" refers to an alkoxy group substituted with 1 to 3 halogens.

As used herein, the term "alkenyl" refers to an ethylenically unsaturated hydrocarbon group, straight or branched, generally having a chain length of 2 to 12 carbon atoms and 1 or 2 ethylenic bonds. The term "haloalkenyl" refers to an alkenyl group substituted with 1 to 3 halogen atoms. The term "alkynyl" refers to an unsaturated hydrocarbon group, straight or branched, generally having a chain length of 2 to 12 carbon atoms and 1 or 2 acetylenic bonds.

The term "cycloalkyl" refers to a saturated ring system having 3 to 7 carbon atoms.

The term "aryl" is understood to be phenyl or napthyl, which may be further substituted with up to three substituents selected from the group consisting of halogen, cyano, nitro, halomethyl, phenyl, phenoxy, ($C_1$–$C_4$)alkyl, ($C_1$–$C_4$) alkylthio, ($C_1$–$C_4$)alkylsulfoxide, ($C_1$–$C_6$)alkoxy and halo ($C_1$–$C_4$)alkyl.

Typical aryl substituents include but are not limited to 4-chlorophenyl, 4-fluorophenyl, 4-bromophenyl, 2-methoxyphenyl, 2-methylphenyl, 3-methyphenyl, 4-methylphenyl, 2,4-dibromophenyl, 3,5-difluorophenyl, 2,4,6-trichlorophenyl, 4-methoxyphenyl, 2-chloronapthyl, 2,4-dimethoxyphenyl, 4-(trifluoromethyl)phenyl and 2-iodo-4-methylphenyl.

The term "heterocyclic" refers to: a substituted or unsubstituted 5 or 6 membered unsaturated ring containing one, two, or three heteroatoms, preferably one or two heteroatoms selected from oxygen, nitrogen, and sulfur; or a bicyclic unsaturated ring system containing up to 10 atoms including one heteratom selected from oxygen, nitrogen, and sulfur. Examples of heterocyclic groups are, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from ($C_1$–$C_4$)alkyl, halogen, cyano, nitro, and halomethyl.

The term "aralkyl" is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifiluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chloro-phenyl)ethyl, 2-(3-chlorophenyl) ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methylphenyl)-ethyl, 2-(4-methylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2,4-dichlorophenyl)ethyl, 2-(3,5-dimethoxy phenyl)ethyl. Typical phenpropyl moieties are 3-phenylpropyl, 3-(2-chlorophenyl)-propyl, 3-(3-chlorophenyl)propyl, 3-(4-chlorophenyl)propyl, 3-(2,4dichlorophenyl)propyl, 3-(2-fluorophenyl)propyl, 3-(3-fluorophenyl)propyl, 3-(4-fluorophenyl)propyl, 3-(2-methylphenyl)-propyl, 3-(3-methylphenyl)propyl, 3-(4-methylphenyl)ethyl, 3-(2-methoxyphenyl)propyl, 3-(3-methoxyphenyl)propyl, 3-(4-methoxyphenyl)propyl, 3-(4-trifluoromethylphenyl)propyl, 3-(2,4-dichlorophenyl)propyl and 3-(3,5-dimethoxyphenyl)propyl. Typical phenbutyl moieties are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methyl-phenyl)butyl, 4-(3-methylphenyl)-butyl, 4-(4-methylphenyl)butyl, 4-(2,4-dichlorophenyl)butyl, 4-(2-methoxphenyl)butyl, 4-(3-methoxyphenyl)butyl and 4-(4-methoxyphenyl)butyl.

Halogen or halo is defined as iodo, fluoro, bromo, and chloro moieties. Those skilled in the art will recognize the double bond between $R_1$ and $R_2$ can exist as cis or trans isomers. These isomers can be separated into individual components by conventional means. Both the individual isomeric compounds and mixtures thereof form subjects of the invention and have fungicidal properties.

The C=C double bond substituents of the benzyloxy fragment in the novel compounds of the general Formula I may be obtained in preparation as E/Z isomeric mixtures. These isomers can be separated into individual components by conventional means. Both the individual isomeric compounds and mixtures thereof form subjects of the invention and have fungicidal properties.

The present invention also includes salts and complexes of Formula (I), the preparation of which would be obvious to one skilled in the art. Further, one skilled in the art will recognize that, by well known methods, substituents can be added to the compound shown in Formula (I) which would, either alone or in combination with the remainder of Formula (I), include one or more asymmetric carbon atoms. It should be recognized that the present invention includes these compounds, as well as their stereoisomers (enantiomorphs).

As used throughout this invention the structures are defined to include the cis/trans and E/Z isomeric mixtures.

A preferred embodiment of this invention are the compounds, enantiomorphs, salts and complexes of Formula (I) where:

$R_1$ and $R_2$ are hydrogen;

$R_3$ is methyl;

R is $(C_1-C_{12})$alkyl, $(C_3-C_7)$cycloalkyl, or phenyl, where the phenyl is substituted with preferably one or two substituents independently selected from halo, halomethyl, cyano, $(C_1-C_4)$alkyl, $(C_1-C_4)$alkylthio, $(C_1-C_4)$alkoxy and phenyl; and the $OCH_2(2-N(OR_3)CO_2CH_3$-aryl) is bonded at the meta position to the $(C=O)_n$—C=C—$(C=O)_m$—R substituent of the phenyl ring as shown below.

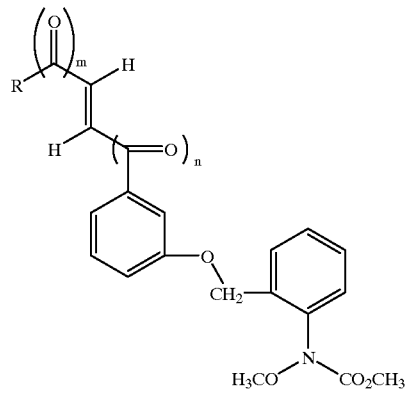

(I')

A more preferred embodiment of this invention are the compounds, enantiomorphs, salts, and complexes of the compound shown in Formula (I') where X is hydrogen and R is t-butyl, n-propyl, halophenyl or cyclopropyl.

Typical compounds encompassed by the present invention of Formula I include those compounds presented in Table 1 of Formula II, III, and IV.

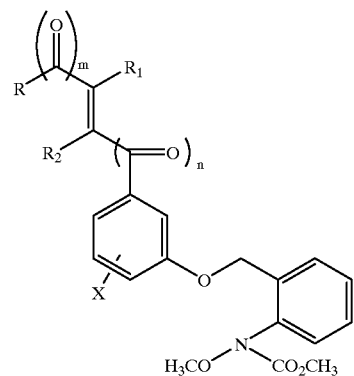

(II)

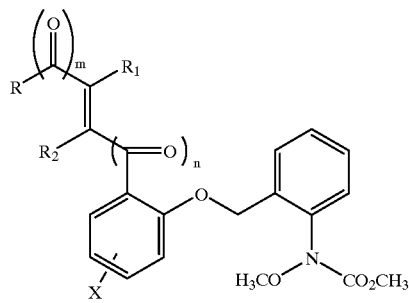

(III)

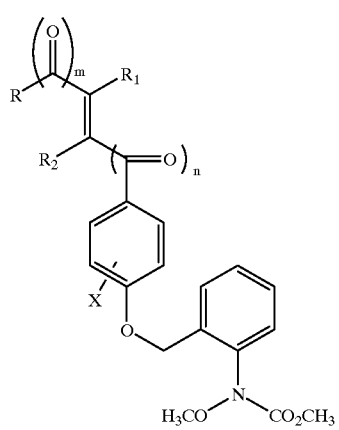

(IV)

In Table 1, for compounds 1.01–1.65, $R_1$ and $R_2$=H, n=0, m=1, and X=H. The other substituents are defined in the table below.

TABLE 1

| Cmpd # | R | Formula |
|---|---|---|
| 1.01 | Ph | II |
| 1.02 | Ph | III |
| 1.03 | Ph | IV |
| 1.04 | 2-Cl(Ph) | II |
| 1.05 | 2-Cl(Ph) | III |
| 1.06 | 2-Cl(Ph) | IV |
| 1.07 | 3-Cl(Ph) | II |
| 1.08 | 3-Cl(Ph) | III |
| 1.09 | 3-Cl(Ph) | IV |
| 1.10 | 4-Cl(Ph) | II |
| 1.11 | 4-Cl(Ph) | III |
| 1.12 | 4-Cl(Ph) | IV |
| 1.13 | 2-Br(Ph) | II |
| 1.14 | 3-Br(Ph) | II |
| 1.15 | 4-Br(Ph) | II |
| 1.16 | 2-F(Ph) | II |
| 1.17 | 3-F(Ph) | II |
| 1.18 | 4-F(Ph) | II |
| 1.19 | 2-OCH$_3$(Ph) | II |
| 1.20 | 3-OCH$_3$(Ph) | II |
| 1.21 | 4-OCH$_3$(Ph) | II |
| 1.22 | 2-CH$_3$(Ph) | II |
| 1.23 | 3-CH$_3$(Ph) | II |
| 1.24 | 4-CH$_3$(Ph) | II |
| 1.25 | 2-CF$_3$(Ph) | II |
| 1.26 | 3-CF$_3$(Ph) | II |
| 1.27 | 4-CF3(Ph) | II |
| 1.28 | 2-NO$_2$(Ph) | II |
| 1.29 | 3-NO$_2$(Ph) | II |
| 1.30 | 4-NO$_2$(Ph) | II |
| 1.31 | 2,4-Cl(Ph) | II |
| 1.32 | 2,5-Cl(Ph) | II |
| 1.33 | 2,4-F(Ph) | II |
| 1.34 | 2,5-F(Ph) | II |
| 1.35 | 3,4-F(Ph) | II |
| 1.36 | CH$_3$ | II |
| 1.37 | CH$_2$CH$_3$ | II |
| 1.38 | CH$_2$CH$_2$CH$_3$ | II |
| 1.39 | CH(CH$_3$)$_2$ | II |
| 1.40 | CH$_2$(CH$_2$)$_3$CH$_3$ | II |
| 1.41 | CH$_2$(CH$_2$)$_4$CH$_3$ | II |
| 1.42 | CH$_2$CH(CH$_3$)$_2$ | II |
| 1.43 | CH(CH$_3$)CH$_2$CH$_3$ | II |
| 1.44 | C(CH$_3$)$_3$ | II |
| 1.45 | CH$_2$C(CH$_3$)$_3$ | II |
| 1.46 | CH(CH$_3$)CH$_2$CH$_2$CH$_3$ | II |
| 1.47 | C(CH3)$_2$CH$_2$CH$_3$ | II |
| 1.48 | CF$_3$ | II |

TABLE 1-continued

| Cmpd # | R | Formula |
|---|---|---|
| 1.49 | CF$_2$CF$_3$ | II |
| 1.50 | CH$_2$CF$_3$ | II |
| 1.51 | CH=CH$_2$ | II |
| 1.52 | cyclopropyl | II |
| 1.53 | cyclopentyl | II |
| 1.54 | cyclohexyl | II |
| 1.55 | CH$_2$OCH$_3$ | II |
| 1.56 | CH$_2$OCH$_2$CH$_3$ | II |
| 1.57 | CH$_2$CH$_2$OCOPh | II |
| 1.58 | CH$_2$OCH$_2$Ph | II |
| 1.59 | 2-pyridyl | II |
| 1.60 | 3-pyridyl | II |
| 1.61 | 2-pyrimidyl | II |
| 1.62 | 4-pyrimidyl | II |
| 1.63 | 2-thienyl | II |
| 1.64 | 3-thienyl | II |
| 1.65 | 2-napthyl | II |

Further typical compounds described by the present invention are described below.

TABLE 2

Compounds 2.1 to 2.65 are Compounds of Table 1 of Formula II, III, IV where in n=1, m=0, and $R_1$ and $R_2$ are H.

TABLE 3

Compounds 3.1 to 3.65 are Compounds of Table 1 of Formula II, III, IV where in n=0, m=1, $R_1$=CH$_3$, and $R_2$ is H.

TABLE 4

Compounds 4.1 to 4.65 are Compounds of Table 1 of Formula II, III, IV where in n=1, m=0, $R_1$=H, and $R_2$ is CH$_3$.

As used herein, "Ph" is understood to be phenyl.

The compounds of Formula I are prepared in a two step sequence. Scheme A describes the preparation of compounds of the formula (I) where n=0 and m=1. The α,β unsaturated compounds (V) can be prepared by conventional condensation techniques. For example *Organic Reactions*, Volume 16 describes the general aldol condensation and specifically the condensation of benzaldehydes with ketones. A hydroxybenzaldehyde is condensed with a ketone, RCOCH$_2$R$_1$. When R$_1$=H the ketone is a methyl ketone, the reaction results in the unsaturated intermediate V'.

Scheme A:

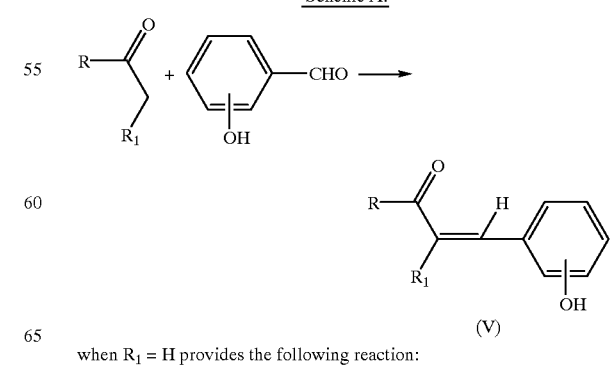

when R$_1$ = H provides the following reaction:

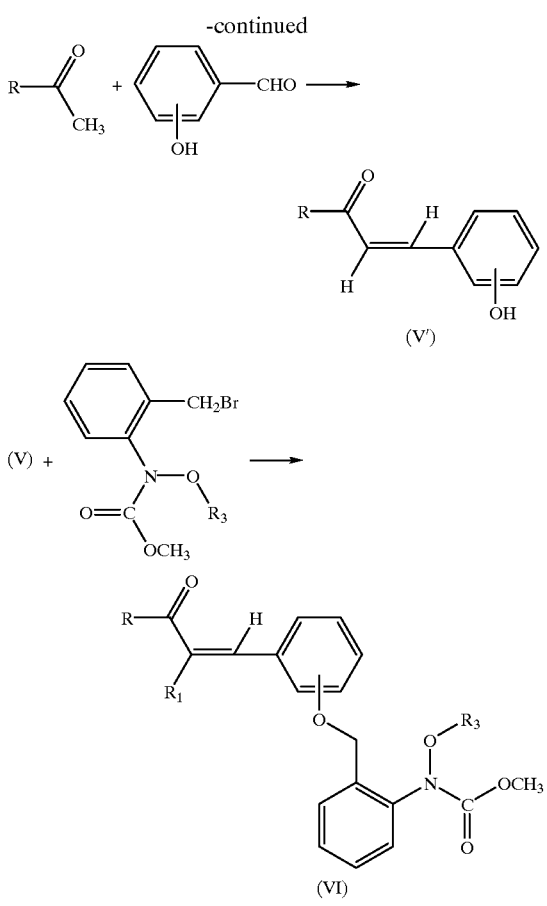

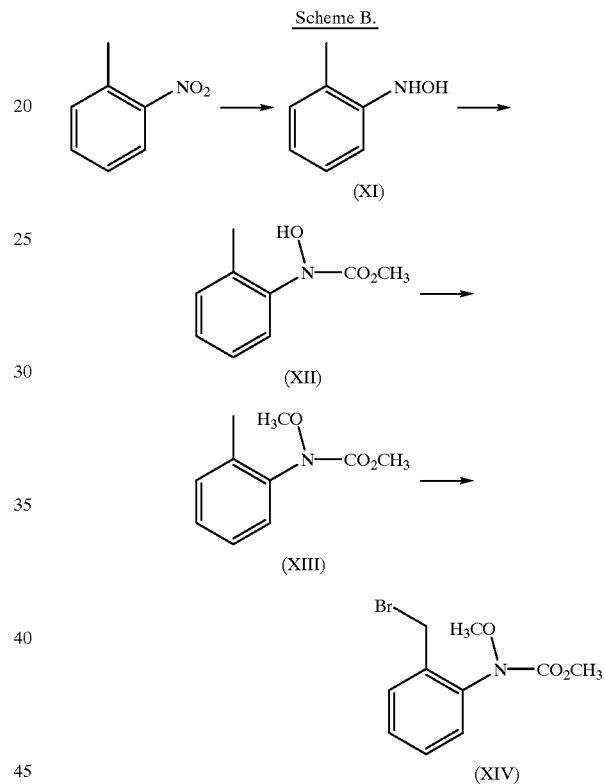

Substituted hydroxybenzaldehyde such as ortho, meta or para-hydroxybenzaldehyde provides three regioisomeric intermediates corresponding to V and V'. A variety of reaction conditions can be employed to prepare the enones (V and V') which are described in *Organic Reactions* Vol. 16 pp. 69–85. For example, a ketone is dissolved in a hydroxylic solvent, such as ethanol, to which is added dropwise a solution of the hydroxybenzaldehyde in an aqueous basic solution. The bases used can be alkali metal hydroxides, such as potassium or sodium hydroxide and the dropwise addition is conducted from 0° C. to 35° C. preferably at ambient temperature.

Compounds of formula (VI) are prepared by the alkylation of intermediate V and V' with the appropriately substituted benzyl bromide. Alkylation of intermediate V' derived from meta-hydroxybenzaldehyde provides compounds of Table 1 of Formula II (wherein $R_1=R_2=H$). Alkylation of intermediate V, wherein $R_1=CH_3$ and $R_2=H$, derived from meta-hydroxybenzaldehyde provides compounds where n=0 and m=1 of Table 3 of Formula II. Alkylation of intermediate V' derived from ortho-hydroxy-benzaldehyde provides compounds of Table 1 of Formula III (wherein $R_1=R_2=H$). Alkylation of intermediate V, wherein $R_1=CH_3$ and $R_2=H$, derived from ortho-hydroxybenzaldehyde provides compounds of Tables 3 of Formula III. Alkylation of intermediate V' derived from para-hydroxybenzaldehyde provides compounds of Table 1 of Formula IV (wherein $R_1=R_2=H$). Alkylation of intermediate V, wherein $R_1=CH_3$ and $R_2=H$, derived from para-hydroxybenzaldehyde provides compounds of Tables 3 of Formula IV.

The 2-N(OR$_3$)CO$_2$CH$_3$-benzylbromide, methyl N-(2-bromomethylphenyl)-N-alkoxycarbamate, is prepared as described in both EP619301 and EP704430 in a 4 step sequence as shown in scheme B. As described in the aforementioned European patent applications o-nitrotoluene is reacted with ammonium chloride in the presence of zinc to provide N-2-methylhydroxylamine (XI) as described in *Organic Synthesis Collective Volume* III, p.668. The hydroxylamine is acylated with methyl chloroformate to provide the methyl N-hydroxycarbamate (XII) which is alkylated, for example with dimethylsulfate (R is methyl), to provide (XIII) which is brominated under standard conditions such as N-bromosuccinimide in carbontetrachloride in the presence of a catalyst such as benzoyl peroxide to afford the intermediate benzylbromide (XIV).

Scheme C describes the preparation of compounds of the formula (1) where n=1 and m=0. The α,β unsaturated compounds (VII) can be prepared by conventional condensation techniques as is in scheme C. A benzaldehyde is condensed with a hydroxyphenylketone, (OH)PhCOCH$_2$R$_2$, which when $R_2=H$ a methyl ketone, provides the unsaturated intermediate VII'.

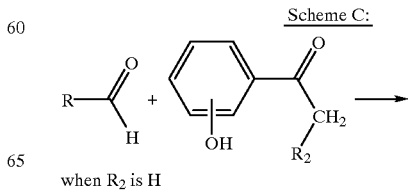

when $R_2$ is H

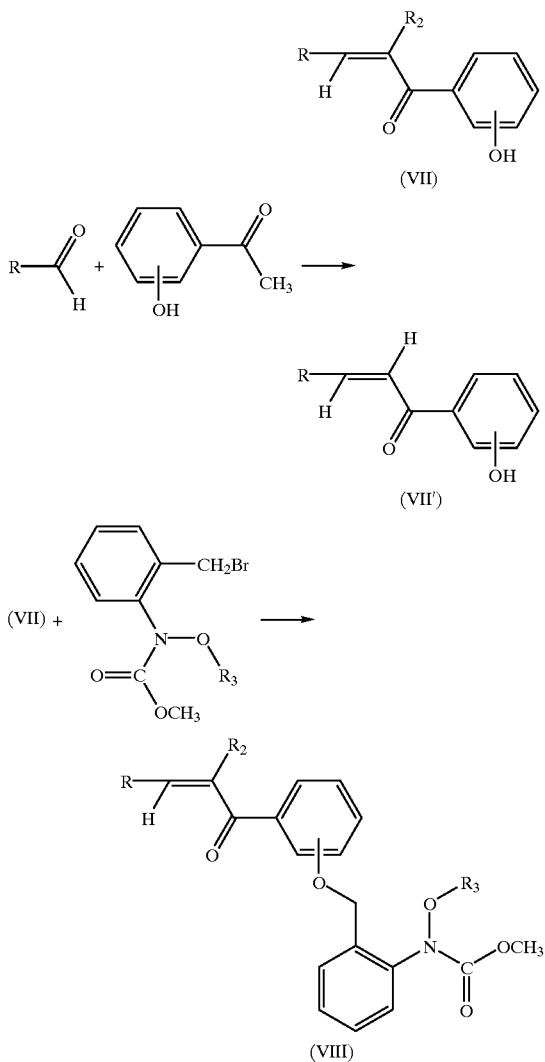

Substituted hydroxyphenylketones such as ortho, meta or para-hydroxyacetophenone provides three regioisomeric intermediates VII' wherein $R_2$ is H. A variety of reaction conditions can be employed to prepare the enones VII and VII' and are described in Organic Reactions Vol. 16 pp. 69–85. For example, to the hydroxyphenylketone and aldehyde in a hydroxylic solvent, such as ethanol, is added a hydroxide base such as barium, sodium or potassium hydroxide. The reaction mixture is stirred at reflux when using barium hydroxide while with sodium or potassium hydroxide the reaction is conducted from 0° C. to 35° C. preferably at ambient temperature. After neutralization the product is isolated by conventional methods.

Compounds of formula VIII are prepared by the alkylation of intermediate VII and VII' with the appropriately substituted benzyl bromide. Alkylation of intermediate VII' derived from meta-hydroxyacetophenone provides compounds of Table 2 of Formula II (wherein $R_1=R_2=H$). Alkylation of intermediate VII, wherein $R_2=CH_3$, derived from meta-hydroxypropiophenone provides compounds of Table 4 of Formula II. Alkylation of intermediate VII' derived from ortho-hydroxyacetophenone provides compounds of Tables 2 of Formula III (wherein $R_1=R_2=H$). Alkylation of intermediate VII, wherein $R_2=CH_3$, derived from ortho-hydroxypropiophenone provides compounds of Table 4 of Formula III. Alkylation of intermediate VII' derived from para-hydroxyacetophenone provides compounds of Table 2 of Formula IV (wherein $R_1=R_2=H$). Alkylation of intermediate VII, wherein $R_2=CH_3$, derived from para-hydroxypropiophenone provides compounds of Table 4 of Formula IV.

The following examples are illustrative of the present invention.

EXAMPLE 1

Methyl N-methoxy-N-[2-(3-(3'-phenyl-3'-oxo-prop-1'-enyl)phenoxymethyl)phenyl]carbamate (Compound 1.01, Table 1).

Into a 250 ml single neck round bottom flask was added 1.5 g (6.7 mmole, 1.0 equiv.) 3-hydroxychalcone in 12 ml DMF and 0.43 g (87%, 6.7 mmole, 1.0 equiv.) powdered KOH pellets. This was stirred for 1 h at ambient conditions. With a pipette, 2.6 g (70%, 6.7 mmole, 1.0 equiv.) methyl N-2-bromomethylphenyl-N-methoxycarbamate in 8 ml DMF was added to the conditions and monitored by gas chromatograph. After 2 h quenched the reaction and worked up: added ether—water and washed with water. The organic phase was dried over anhydrous magnesium sulfate, and rotovaped to remove the solvent at 50° C. to give 2.9 g of crude product as an orange oil.

The crude product was purified by flash chromatography to give a mixture of product and chalcone. Ethyl acetate was added to the mixture which was then washed with 10% NaOH soln. and further washed with water. The organic phase was dried over anhydrous magnesium sulfate, and rotovaped to remove the solvent at 50° C. to give 1.4 g of methyl N-methoxy-N-[2-(3-(3'-phenyl-3'-oxo-prop-1'-enyl) phenoxymethyl)phenyl]carbamate product as a light yellow oil (50.1% yield).

Elemental Analysis: theoretical % / found % C: 71.94/ 71.34 H: 5.51/5.75 N: 3.35/3.14 O: 19.18/20.10; NMR (300 MHz): 3.76 (s, 3H), 3.82 (s, 3H), 5.17 (s, 2H), 7.26–8.02 (m, 15H).

Preparation of 3-hydroxychalcone (used in the preparation of the compound 1.01 in Example 1).

To a 250 ml round bottom flask equipped with magnetic stirrer and side arm addition funnel was charged 12.0 g (0.10 moles) of acetophenone and 50 ml of absolute ethanol. In 50 ml of water was dissolved 3-hydroxybenzaldehyde (12.2 g, 0.10 moles) and 6.4 g of 86% potassium hydroxide (0.10 moles) and this was added dropwise to the stirring solution of acetophenone, at room temperature. The reaction was stirred at ambient temperature overnight, then poured into 250 ml. of water, and acidified to pH 2 with 1 N aqueous hydrochloric acid. A light yellow precipitate formed, which was collected by vacuum filtration, washed with water, and dried in vacuo at 40° C. overnight. A total of 17 g (76.9% yield) of product, 3-hydroxychalcone, was isolated as a tan solid. MP=162–164° C.

EXAMPLE 2

Methyl N-methoxy-N-[2-(3-(3'-phenyl-1'-oxo-prop-3'-en-yl)phenoxymethyl)phenyl]carbamate (Compound 2.01, Table 2).

Into a 100 ml RBF was added 1.0 g (4.46 mmole, 1.0 equiv.) 3'-hydroxychalcone in 10 ml DMF and 0.29 g (87%, 4.46 mmole, 1.0 equiv.) powdered KOH pellets. The mixture was stirred for 15 minutes. With a pipette, 2.1 g (70%, 4.46 mmole, 1.0 equiv.) methyl N-2-bromomethylphenyl-N- methoxycarbamate in 5 ml DMF was added to the reaction mixture causing a slight release of heat. The mixture was stirred for 17 hours at room temperature and monitored by thin layer chromatography. Worked up after 17 hours with ethyl acetate—water, washed with 10% NaOH solution, and further washed with water. The organic phase was dried over anhydrous magnesium sulfate, and rotovaped under vacuum at 50° C. to give 2.4 g oil crude product.

This crude product was purified using flash chromatography to give 0.6 g of product as a brown oil in fraction #6 and slightly less pure product 0.86 g of brown oil in fractions #5, 7, 8 for a total of 1.46 g of methyl N-methoxy-N-[2-(3-(3'-phenyl-1'-oxo-prop-3'-en-yl)phenoxy-methyl)phenyl] carbamate product as a brown oil (79.6% yield).

NMR (300 MHz): 3.76(s, 3H), 3.80 (s, 3H), 5.19 (s, 2H), 7.2–7.6 (m, 15H).

Preparation of 3'-hydroxychalcone (used in the preparation of the compound 2.01 in Example 2).

To a 250 ml round bottom flask equipped with a magnetic stirrer and reflux condenser, was charged 2.7 g (0.02 moles) of 3-hydroxyacetophenone, 2.1 g (0.02 moles) of benzaldehyde, 2.0 g (0.011 moles) of barium hydroxide, monohydrate, and 20 ml of absolute ethanol. The reaction mixture was refluxed for a total of 2.5 hours, after which it became thick and difficult to stir. Upon cooling, the resulting solid was dissolved in 100 ml. of 1 N aqueous hydrochloric acid, and another solid was observed to precipitate from this solution. The solid was collected by vacuum filtration, and washed with 100 ml. of water, then 100 ml. of hexane and dried in vacuuo at 40° C. for 24 hours. As a result, 4.2 g (93% yield) of 3'-hydroxychalcone was isolated as a tan solid, MP=143–147° C.

EXAMPLE 3

Numerous compounds of this invention were tested for fungicidal activity in vivo against the diseases described below. The compounds were dissolved in a 2:1:1 mixture of water, acetone and methanol (by volume), sprayed onto the plants, allowed to dry (two hours) and then the plants were inoculated with fungal spores. Each test utilized control plants which were sprayed with the water, acetone and methanol mixture and inoculated. The remainder of the technique of each of the tests is given below along with the results for various compounds described herein by the Compound # against the various fungi at a dose of 300 grams per hectare. The results are reported as percent disease control, compared to the control wherein one hundred was rated as total disease control and zero as no disease control. The application of the fungi to the test plants was as follows:

Wheat Leaf Rust (WLR)

*Puccinia recondita* (f. sp. tritici) was cultured on 7 day old wheat (cultivar Fielder) over a 12 day period in the greenhouse. Spores were collected from the leaves by settling on aluminum foil. The spores were cleaned by sieving through a 250 micron opening screen and stored or used fresh. Storage employed sealed bags in an Ultralow freezer. A spore suspension was prepared from dry uredia by adding 20 mg (9.5 million spores) per ml. of Soltrol oil. The suspension was dispensed into gelatin capsules (0.7 ml. capacity) which attach to the oil atomizers. One capsule is used per flat of twenty 2 inch square pots of 7 day old Fielder wheat. After waiting for at least 15 minutes for the oil to evaporate from the wheat leaves, the plants were placed in a dark mist chamber (18–20° C. and 100% relative humidity) for 24 hours. The plants were then put in the greenhouse for the latent period and scored after 12 days for disease levels. For protective tests the plants are inoculated one day after spraying the plants with the fungicide compounds.

Wheat Leaf Blotch (SNW)

Cultures of *Septoria nodorum* were maintained on Czapek-Dox V-8 juice agar plates in an incubator at 20° C. with alternating periods of 12 hours of light and 12 hours of darkness for 3 weeks. A water suspension of the spores was obtained by shaking the portion of the plate with fungal material in deionized water and filtering through cheesecloth. The spore-containing water suspension was diluted to a spore concentration of $3.0\times10^6$ spores per ml. The inoculum was dispersed by a DeVilbiss atomizer over one week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

*Erysiphe graminis* (f. sp. tritici) was cultured on wheat seedlings in a controlled temperature room at 18° C. Mildew spores were shaken from the culture plants onto 7 day old wheat seedlings which had been previously sprayed with the fungicide compound. The inoculated seedlings were kept in a controlled temperature room at 18° C. and subirrigated. The percent disease control was rated 7 days after the inoculation.

Cucumber Powdery Mildew (CPM)

*Sphaerotheca fulginea* was maintained on cucumber plants, cv. Bush Champion, in the greenhouse. Inoculum was prepared by washing the spores from the leaves with water which had 1 drop of Tween 80 per 100 ml. After shaking the plants, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Tomato Late Blight (TLB)

Cultures of *Phytophthora infestans* were maintained on green pea-amended agar for two to four weeks. The spores were washed from the agar with water and dispersed by DeVilbiss atomizer over the leaves of 3-week old Pixie tomato plants which had been sprayed previously with experimental fungicides. The inoculated plants were placed in a humidity cabinet at 20° C. for 24 hours for infection. The plants were then removed to a controlled environment room at 20° C. The plants were scored for disease control after five days.

Grape Downy Mildew (GDM)

*Plasmopara viticola* was maintained on leaves of live grape plants, cv.

Delaware, in a controlled temperature chamber at 20° C. in humid air with moderate light intensity for 7 to 8 days. A water suspension of the spores from infested leaves was obtained and the spore concentration was adjusted to about $3\times10^5$ per ml of water. Delaware grape plants were inoculated by spraying the underside of leaves with a DeVilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

TABLE 2

| Compound | WLR | SNW | WPM | CPM | TLB | GDM |
|---|---|---|---|---|---|---|
| 1.01 | 80 | 80 | 50 | 50 | 90 | 95 |
| 2.01 | 80 | 80 | nt* | 50 | 90 | 95 |

*not tested

All numbers indicate minimum degree of control, e.g., compounds 1.01 and 2.01 provided 80% or better control against wheat leaf rust.

The compounds of this invention are useful as agricultural fungicides and, as such, can be applied to various loci such as the seed, the soil or the foliage.

The compounds of this invention can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protector, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15).

The compounds of this invention can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse, or diffuse the active ingredient in the composition without impairing the effectiveness of the active ingredient and which substance by itself has no significant detrimental effect on the soil, equipment, desirable plants, or agronomic environment. If desired, adjuvants such as surfactants, stabilizers, antifoam agents and anti-drift agents may also be combined.

Examples of compositions and formulations according to the invention are aqueous solutions and dispersions, oily solutions and oil dispersions, pastes, dusting powders, wettable powders, emulsifiable concentrates, flowables, granules, invert emulsions, and aerosol compositions. Wettable powders, pastes, flowables and emulsifiable concentrates are concentrated preparations which are diluted with water before or during use. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound Formula I, 45 parts of a synthetic precipitated hydrated silicon dioxide, such as that sold under the trademark Hi-SilR, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®3 (which is a precipitated synthetic amorphous sodium magnesium aluminosilicate available from J.M. Huber Corporation of Edison, N.J.).

Dusts are prepared by mixing compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as sprays by methods commonly employed, such as conventional high-gallonage hydraulic sprays, low gallonage sprays, ultra-low-volume sprays, airblast spray, aerial sprays, and dusts.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. Compounds having the structure:

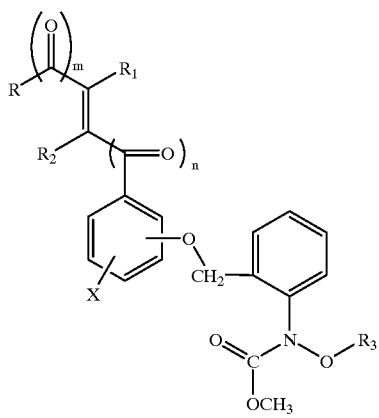

(I)

wherein m and n are integers selected from 0 and 1, provided that m+n is 1;

X is independently selected from hydrogen, halo, $(C_1-C_4)$ alkyl, and $(C_1-C_4)$alkoxy;

R is independently selected from hydrogen, $(C_1-C_{12})$ alkyl, halo$(C_1-C_{12})$alkyl, $(C_2-C_{12})$alkenyl, halo $(C_2-C_{12})$alkenyl, $(C_2-C_{12})$alkynyl, halo$(C_2-C_{12})$ alkynyl, $(C_1-C_{12})$alkoxy$(C_1-C_{12})$alkyl, $(C_3-C_7)$ cycloalkyl, halo$(C_3-C_7)$cycloalkyl, $(C_3-C_7)$cycloalkyl $(C_1-C_4)$alkyl, aryl$(C_3-C_7)$cycloalkyl, aryl, aralkyl, and heterocyclic;

$R_1$ and $R_2$ are independently selected from hydrogen, $(C_1-C_{12})$alkyl, halo$(C_1-C_{12})$alkyl, $(C_3-C_7)$cycloalkyl, $(C_3-C_7)$cycloalkyl$(C_1-C_4)$alkyl, cyano, carboxy $(C_1-C_4)$alkyl, aryl and $R_3$ is independently selected from $(C_1-C_{12})$alkyl and halo$(C_1-C_{12})$alkyl;

provided that at least one of $R_1$ and $R_2$ is hydrogen; and enantiomorphs, salts, and complexes of said compounds.

2. The compounds of claim 1 having the following formula:

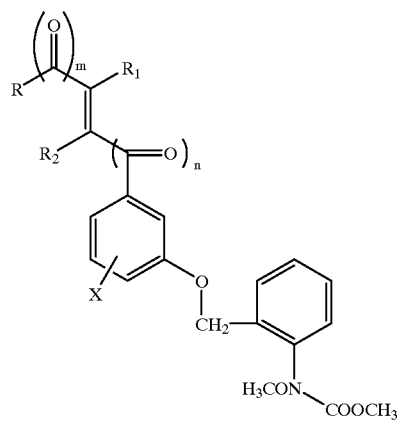

wherein R is selected from the group consisting of $(C_1-C_{12})$alkyl, halo$(C_1-C_{12})$alkyl, $(C_3-C_7)$cycloalkyl, halo-substituted phenyl, $(C_1-C_4)$alkyl substituted phenyl, and halo-alkyl-substituted phenyl.

3. The compound of claim 2 wherein n=0 and m=1.

4. The compound of claim 3 wherein R is selected from the group consisting of $(C_1-C_6)$alkyl, halo$(C_1-C_4)$alkyl, halo$(C_1-C_4)$alkyl phenyl, $(C_3-C_7)$cycloalkyl, 2-halophenyl, 3-halophenyl, 4-halophenyl, 2-$(C_1-C_4)$alkylphenyl, 3-$(C_1-C_4)$alkylphenyl and 4-$(C_1-C_4)$alkylphenyl.

5. The compound of claim 4 wherein $R_1$ and $R_2$ are both hydrogen.

6. The compound of claim 5 wherein R is selected from the group consisting of n-propyl, isopropyl, tert-butyl, n-butyl, n-hexyl, cyclopropyl, 4-fluorophenyl, 4-chlorophenyl, and 4-trifluoromethylphenyl.

7. A fungicidal composition for controlling phytopathogenic fungi which comprises an agronomically acceptable carrier and the compound of claim 1 wherein the weight ratio of the carrier to the compound is 99:1 to 1:4.

8. The composition of claim 7 wherein the weight ratio of the agronomically acceptable carrier to compound is 10:1 to 1:3.

9. A method for controlling phytopathogenic fungi which comprises applying to at least one of a seed, a plant and soil the compound of claim 1 at a rate of from 0.005 to 50 kilograms per hectare.

* * * * *